Figure 1:
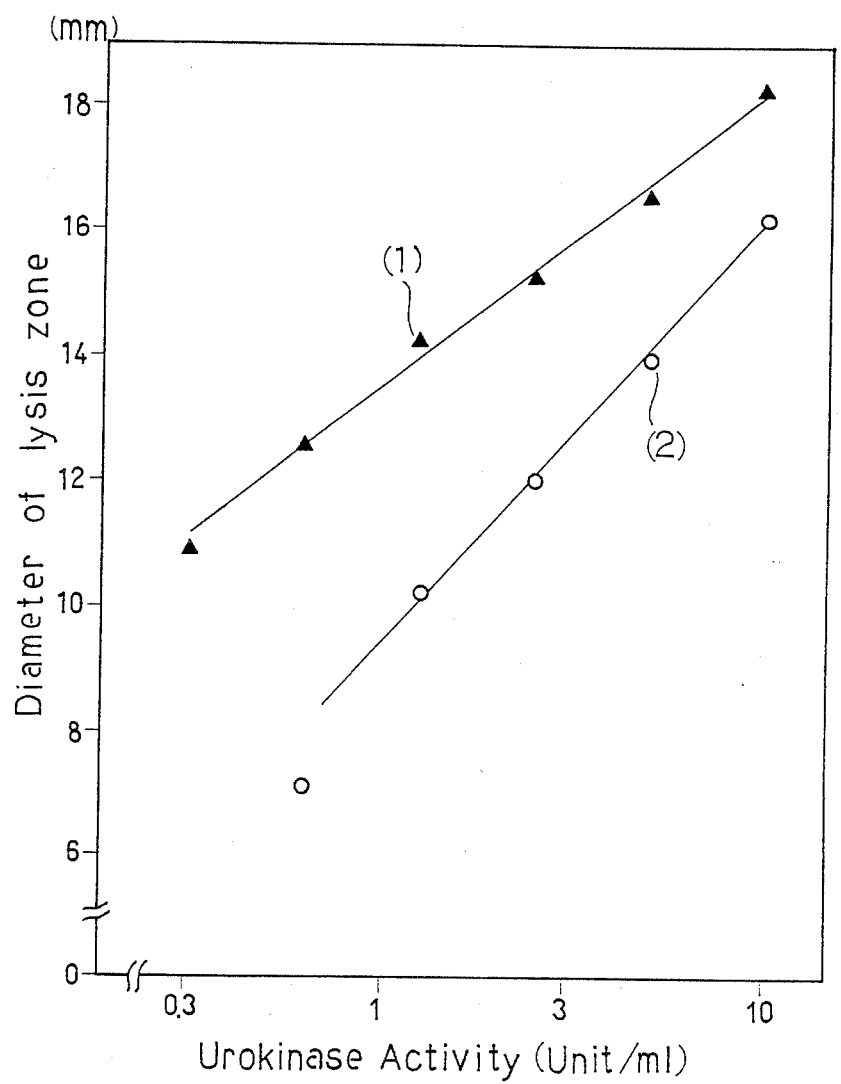

United States Patent [19]

Nakayama et al.

[11] Patent Number: 4,545,988
[45] Date of Patent: Oct. 8, 1985

[54] UROKINASE-PLASMIN COMPLEX ADSORBABLE BY FIBRIN AND PROCESS FOR PREPARING SAME

[75] Inventors: Yasuo Nakayama; Wasei Miyazaki; Masanao Shinohara, all of Tokushima, Japan

[73] Assignee: Otsuka Pharmaceutical Co., Ltd., Japan

[21] Appl. No.: 683,024

[22] Filed: Dec. 18, 1984

[30] Foreign Application Priority Data

Dec. 23, 1983 [JP] Japan ................................ 58-251990

[51] Int. Cl.$^4$ ........................ A61K 37/54; C12N 9/68; C12N 9/72; C12N 9/96
[52] U.S. Cl. ..................................... 424/94; 435/177; 435/181; 435/188; 435/215; 435/217
[58] Field of Search ............... 435/177, 188, 217, 215, 435/181; 424/94

[56] References Cited

U.S. PATENT DOCUMENTS 3,926,727 12/1975 Vairel et al. ..................... 435/188 X
4,082,612 4/1978 Robbins et al. ..................... 435/217
4,272,506 6/1981 Schwarzberg ..................... 424/85 X
4,337,244 6/1982 Smith ..................... 424/94
4,418,052 11/1983 Wong ..................... 260/112 B X

FOREIGN PATENT DOCUMENTS 0109653 5/1984 European Pat. Off. ............ 435/181

OTHER PUBLICATIONS

Biochemistry, 5, 2160-2169, White et al., (1966).
Eur. J. Biochem., 57, 441-451 (1975), Pinck et al.
Fibrinolysis, Academic Press, 1978, Gaffney et al., pp. 77-82.
J. Immunol. Methods, 35, 267-275 (1980), Terouanne et al.
Progress in Chemical Fibrinolysis and Thrombolysis, 3, 191-222 (1978), Sottrup-Jensen et al.
J. Biol. Chem., 258, (13), 8014-8019 (1983), Sumi et al.

Primary Examiner—Howard E. Schain
Attorney, Agent, or Firm—Larson and Taylor

[57] ABSTRACT

This invention provides a urokinase complex adsorbable by fibrin characterized in that it comprises heavy chain of high molecular weight urokinase as coupled with heavy chain of plasmin by one or more S-S bonds and a process for preparing the same.

8 Claims, 1 Drawing Figure

UROKINASE-PLASMIN COMPLEX ADSORBABLE BY FIBRIN AND PROCESS FOR PREPARING SAME

This invention relates to a novel urokinase complex which is adsorbable by fibrin and to a process for preparing the same.

There are two kinds of urokinases obtained from the human urine on purification: the high molecular weight type (which has a molecular weight of about 54,000 and comprises a heavy chain including an active site and having a molecular weight of about 32,000, and a light chain having a molecular weight of about 22,000, the heavy chain being linked to the light chain by an S—S bond) and the low molecular weight type (which comprises a heavy chain with a molecular weight of about 32,000). The low molecular weight type is produced from the high molecular weight type with limited proteolysis during purification [W. F. White et al., Biochemistry, 5, 2160 (1966)]. These two types of urokinases are not greatly different in in vitro enzymatic activity and are widely used clinically as agents for treating thrombosis. However, these urokinases are not capable of being adsorbed by fibrin which is a protein component of thrombi, and, when intravenously given, are rapidly metabolized and excreted, so that the enzymes fail to achieve as high a therapeutic effect as is expected from their activity in vitro. When the urokinase is administered at large doses, systemic activation of plasminogen takes place, accompanied by marked side effects such as a tendency of bleeding due to the decomposition of fibrinogen. Furthermore, the circulating blood contains large amounts of plasmin inhibitors, such as $\alpha_2$-plasmin inhibitor and $\alpha_2$-macroglobulin, which inhibit the thrombolysis by urokinase due to the formation of plasmin or activation of plasminogen.

In view of the above situation, it has been desired to develop more effective thrombolytic agents.

An object of the present invention is to provide a urokinase complex having a thrombolytic activity, adsorbable by fibrin and less likely to be metabolized and excreted rapidly.

Another object of the invention is to provide a process for preparing such a urokinase complex.

The above objects and other features of the invention will become apparent from the following description.

The present invention provides a urokinase complex adsorbable by fibrin characterized in that it comprises heavy chain of high molecular weight urokinase as coupled with heavy chain of plasmin by one or more S—S bonds.

We have carried out intensive research, directing attention to the possibility of coupling a fibrin-adsorbable protein (i.e. a protein adsorbable by fibrin) with urokinase to give urokinase ability to couple with fibrin because the urokinase will then be adsorbed to thrombi as contemplated for therapy with reduced susceptibility to metabolism and excretion to result in a prolonged half-life period thereof in the blood and achieve the desired therapeutic effect. Consequently we have found that the above objects of the invention can be fulfilled by coupling the heavy chain of plasmin, serving as fibrin-adsorbable protein, with the heavy chain of high molecular weight urokinase by one or more S—S bonds. The complex of the present invention acts selectively (locally) on the site of thrombus when used as a thrombolytic agent in a smaller amount than when urokinase is used singly, undergoes retarded metabolism and excretion, is less affected by plasmin inhibitors, exhibits sustained satisfactory thrombolytic activity and is less likely to entail side effects such as tendency of systemic bleeding, hence very effective. Especially, the complex of the present invention has the most natural structure that the heavy chain of high molecular weight urokinase is coupled with the heavy chain of plasmin by one or more S—S bonds without using any coupling reagent, at the site(s) where each heavy chain is originally linked to the counterpart light chain. Moreover, the site where the heavy chain of plasmin is coupled with urokinase by the S—S bond is considered to be irrelevant to the site of exhibition of urokinase activity. The complex therefore exhibits high fibrinolytic (thrombolytic) activity and is useful as a novel thrombolytic agent, contributing a great deal to the pharmaceutical industry and other fields. The present invention further provides a novel process for preparing the novel and useful thrombolytic complex with ease and high efficiency.

The complex of the present invention will be described below in detail with reference to the process for preparing the same.

The present urokinase complex which is adsorbable by fibrin is prepared by coupling the heavy chain of high molecular weight urokinase with the heavy chain of plasmin by one or more S—S bonds using an intermolecular disulfide interchange reaction.

The heavy chain of high molecular weight urokinase to be used for preparing the present complex can be easily separated and produced from known high molecular weight urokinase [HMW-UK, about 54,000 in average molecular weight, Biochemistry, 5, 2160 (1966)]. More specifically, the heavy chain of high molecular weight urokinase can be separated and obtained by subjecting HMW-UK to partial reduction in the presence of a thiol, such as 2-mercaptoethanol, dithiothreitol or dithioerythritol, to reductively cleave the S—S bond between the heavy chain and light chain thereof, and subsequently causing a resin having affinity ligands for the active site of the HMW-UK heavy chain to adsorb the reaction mixture, followed by elution [H. Sumi and K. C. Robbins, J. Biol. Chem., 258(13) 8014 (1983)]. The heavy chain of high molecular weight urokinase thus isolated will hereinafter be referred to as "HMW-UK-SH".

The plasmin heavy chain to be used for preparing the present complex is produced, for example, by the process disclosed in Eur. J. Biochem., 57, 441 (1975) or the like and has mercapto groups obtained by subjecting plasmin to partial reduction. Plasmin, which is a blood protein, has high ability to be adsorbed by fibrin, and the adsorption sites have been clarified considerably in detail [B. Wiman and P. Wallen, Thrombosis Research, 1, 213 (1977)]. More specifically, human plasmin is a protein having a molecular weight of about 90,000 and comprising a heavy chain (about 60,000 in molecular weight) participating in its adsorption by fibrin, and a light chain (about 30,000 in molecular weight) including an active site and coupled to the heavy chain by two S—S bonds. It is known that the heavy chain has five closely resembling, repeating, unitary structures (termed "Kringle"s) and that Kringles 1 to 3 have a site which is highly adsorbable by fibrin, Kringle 4 also being adsorbable by fibrin [L. Sottrup-Jensen et al., Progress in Chemical Fibrinolysis and Thrombolysis, 3, 191 (1978)]. The plasmin heavy chain can be separated and obtained in the same manner as above, i.e. by subjecting plasmin to partial reduction in the presence of 2-mercaptoethanol to cleave the S—S bonds between the heavy chain and the light chain, and causing the reaction mixture to be adsorbed by lysine-Sepharose or the like having affinity only for the heavy chain, followed by elution.

The high molecular weight urokinase heavy chain and plasmin heavy chain thus obtained can be coupled together, for example, by an intermolecular disulfide interchange reaction [Terouanne, B., Nicolas, J. C., Descomps, B. and Crustes de Paulet, A., J. Immunol. Methods, 35, 267 (1960)]. The intermolecular disulfide interchange reaction is carried out in an aqueous solution, for example, in physiological saline or usual buffer having a pH of about 4 to about 10, preferably in a buffer having a pH of about 6 to about 8, at about 0° to about 40° C., preferably around room temperature. It is desirable to conduct the reaction in a nitrogen stream. The reaction is completed usually in several minutes to about 24 hours. The buffer to be used can be any of those heretofore known, for example, phosphate buffer, Tris buffer, Hepes buffer, etc. More preferably the coupling reaction is conducted by causing a large excess of 5,5'-dithio-bis(2-nitrobenzoic acid) to act on the heavy chain of high molecular weight urokinase (HMW-UK-SH) to add 3-carboxy-4-nitrophenylthio group to the mercapto group of the cystein residue which has originally participated in coupling the heavy chain with the light chain, thereby giving a 3-carboxy-4-nitrophenylthio group-attached heavy chain of high molecular weight urokinase [HMW-UK-S-S-(3-carboxy-4-nitrophenyl)]. Then the plasmin heavy chain is reacted therewith. During the reaction, the 3-carboxy-4-nitrophenylthio group is eliminated, with the result that the desired S—S bond(s) is(are) formed between the urokinase heavy chain and the plasmin heavy chain.

While the ratio of the high molecular weight urokinase heavy chain with or without 3-carboxy-4-nitrophenylthio group attached thereto and the plasmin heavy chain to be used for the coupling reaction is suitably determined, usually about 0.5 to about 10 moles, preferably about 1 to about 5 moles, of the plasmin heavy chain is used per mole of the high molecular weight urokinase heavy chain or 3-carboxy-4-nitrophenylthio group-attached heavy chain of high molecular weight urokinase.

The complex of the present invention thus prepared generally comprises 1 mole of plasmin heavy chain and about 1 to about 3 moles, preferably about 1 mole, of high molecular weight urokinase heavy chain coupled therewith. This can be confirmed from the molecular weight of the complex obtained and also from the result obtained by reducing the complex and subjecting the reduction products to electrophoresis after treatment with SDS, i.e. from the numbers of active SH groups possessed by the reduction products corresponding to the bands obtained. Stated specifically, the complex reduced as above (for cleavage of the S—S bond(s)) exhibits a band at a molecular weight of about 60,000 as well as a band at a molecular weight of about 30,000. The reduction product corresponding to the band with a molecular weight of about 60,000 has three SH groups on the average, while reduction product corresponding to the band with a molecular weight of about 30,000 has one SH group on the average. On the other hand, the plasmin heavy chain has two SH groups resulting from the reduction cleavage of the two S—S bonds between the heavy chain and the plasmin light chain and further has one more SH group on the average. The high molecular weight urokinase heavy chain has one SH group resulting from the reduction cleavage of the S—S bond between the heavy chain and the light chain. Accordingly the present complex is produced by the coupling of the SH groups of the two heavy chains.

After the coupling reaction, the complex of the invention can be easily isolated and purified by a usual method such as dialysis, gel filtration, fractional precipitation or affinity chromatography. The complex can be preserved when freeze-dried by the usual method.

The complex obtained by the present process is adsorbable by fibrin, has urokinase activity and is effective as a thrombolytic agent for treating thrombosis.

For use as a thrombolytic agent, the complex is formulated into pharmaceutical compositions with use of usual pharmaceutically acceptable, non-toxic carriers.

The thrombolytic composition can be in any of various dosage forms in accordance with the contemplated purpose of treatment. It is used usually as an injection which is sterilized by the usual method and preferably made isotonic with the blood. The injection can be prepared with use of various diluents which are generally used in the art and which include, for example, water and saline. In this case, the injection may contain common salt, glucose or glycerin in an amount sufficient to form an isotonic solution. The thrombolytic composition may have incorporated therein a usual auxiliary solubilizer, buffer, analgesic, preservative and, when desired, coloring agent, perfume, flavoring, sweetener, other drug, etc.

Although the amount of the present complex to be contained in the thrombolytic composition is not limited particularly but is suitably variable over a wide range, it is usually about 0.01 to about 30% by weight of the whole composition.

The thrombolytic composition is not specifically limited in the mode of administration and can be given by a suitable method in accordance with the particular form of the composition. Usually it is given in the form of an injection to mammals including humans, intravenously, singly or as admixed with a glucose, amino acid or like parenteral solution. The dose for human patients, which is suitably determined according to the purpose, symptoms, etc., is usually about 1,000 to about 500,000 units/kg body weight/day calculated as the effective component, i.e., urokinase complex of the invention. The composition may be given in two to four divided doses daily.

Given below are Reference Examples for preparing high molecular weight urokinase heavy chain and plasmin heavy chain to be used for the invention, Examples for preparing complexes of the invention and Pharmacological Test Examples for the complexes obtained in Examples. The complex was tested for activities and other properties by the following methods.

DETERMINATION OF UROKINASE ACTIVITY (1) Synthetic substrate method (Amidolytic activity of urokinase)

A sample of urokinase is diluted to a suitable concentration with an aqueous solution containing 0.15M NaCl and 5 g/liter polyethylene glycol ("PEG 6000", product of Wako Junyaku Co., Ltd., Japan). A 800 μl quantity of 0.05M Tris.HCl buffer (pH=8.4) containing 0.1M NaCl is added to a 100 μl portion of the dilution, and the mixture is heated to 37° C. for 1 minute. A 100 μl quantity of a liquid prepared by adding 0.3 μM of substrate S-2444 (PyroGlu-Gly-Arg-p-Nitroanilide, product of AB kabi, Stockholm, Sweden) to the same buffer as above is added to the above mixture, and the resulting mixture is incubated at 37° C. for 2 minutes. A 100 μl quantity of 50% aqueous solution of acetic acid is added to the mixture to terminate the reaction, and the absorbance of the mixture is measured at 405 nm. The same procedure as above is repeated with use of standard urokinase. The activity of the sample is calculated from the absorbance measurements. The enzyme activity was expressed in International Units against the Japanese Urokinase Standard MM003.

(2) Standard fibrin plate methods (Fibrinolytic activity of urokinase)

To 6 ml of 0.05M Veronal buffer (pH=8.0) containing 0.3% fibrinogen (product of Provite Production B.V., Amsterdam, Holland) and 0.1M NaCl are added final 0.02M $CaCl_2$ and final 3 NIH units/ml of bovine thrombin (product of Mochida Pharmaceutical Co., Ltd., Japan). The mixture is stirred and then scattered over a dish (8.5 cm in inside diameter) to prepare a fibrin plate. A 10 μl quantity of urokinase sample prepared by dissolving 0.1% rabbit serum albumin (product of Sigma Chemical Company, U.S.A.) in the same buffer as above is spotted on the fibrin plate, which is then incubated at 37° C. for 16 hours. The diameter of lysis zone is thereafter measured.

QUANTITATIVE DETERMINATION OF SH GROUP

To 100 μl of deoxygenated sample is added 1 ml of deoxygenated 0.2M Tris.HCl buffer (pH=8.2). To the mixture is added 100 μl of 0.01M 5,5'-dithiobis(2-nitrobenzoic acid) in deoxygenated methanol, the resulting mixture is stirred and then allowed to stand at room temperature for about 30 minutes, and the absorbance thereof is measured at 412 nm. The SH group content of the sample was calculated using 2-mercaptoethanol as a standard.

SDS POLYACRYLAMIDE GEL ELECTROPHORESIS (SDS-PAGE)

A quantity of sample is admixed with the same amount of 0.02M Tris.HCl buffer (pH=8.0) containing 40% glycerol and 2% SDS, and the mixture is heated at 100° C. for 2 minutes. The mixture is subjected to electrophoresis using 12.5% running gel and 4% stacking gel according to the method of U.K. Laemmli et al (Nature (London), 227, 680 (1970)) and using Gradient Gel/PAA 4/30 (product of Pharmacia Fine Chemicals, Sweden). The mixture was thereafter dyed with Coomassie Brilliant Blue (C.B.B.), and the molecular weight was measured using a standard protein (Molecular Weight Kit, product of Pharmacia Fine Chemicals).

REFERENCE EXAMPLE 1

Preparation of high molecular weight urokinase heavy chain

A 2 ml quantity of solution (0.05M Tris.HCl buffer, pH 8.0, containing 0.15M NaCl and 0.002M EDTA) which contained 1,300,000 units (according to synthetic substrate method, the same as hereinafter) of high molecular weight urokinase (product of Japan Chemical Research Co., Ltd., Japan) was deoxygenated, and 2-mercaptoethanol was added to the solution to a final concentration of 0.01M. The mixture was stirred in a nitrogen stream at room temperature for about 10 hours. The reaction mixture was cooled and then passed through Sephadex G-25 fine column (product of Pharmacia Fine Chemicals, 1.5 cm in diameter and 1.5 cm in length) at 4° C. to remove the unreacted mercaptoethanol. The same buffer as above, fully deoxygenated, was used for the equilibration of the column and elution. One ml of the same buffer as above containing 0.01M 5,5'-dithio-bis(2-nitrobenzoic acid) was added to the protein peak fraction (about 9 ml) obtained. The mixture was stirred at room temperature for 30 minutes, then adjusted to a pH of 7.5 with 1N HCl and applied at 4° C. to a column (1.5 cm in diameter and 4 cm in length) of benzamidine-CH-Sepharose (prepared according to the method of L. Holmberg et al (Biochemica et Biophysica Acta, 445, 215 (1976)). The column was equilibrated and washed with deoxygenated 0.05M Tris.HCl buffer (pH 7.5, containing 0.4M NaCl and 0.01M EDTA) and subjected to elution with 0.1M acetic acid containing 0.4M NaCl. The protein peak fraction of the eluate was concentrated by Diaflo ultrafiltration membrane PM-10 (product of Amicon Corporation, U.S.A.) and thereafter dialyzed with deoxygenated 0.01M sodium phosphate buffer (pH 8.0, containing 0.15M NaCl and 0.01M EDTA) at 4° C. The above procedure gave about 1,000,000 units of urokinase (active heavy chain) having a 3-carboxy-4-nitrophenylthio group attached thereto.

The urokinase heavy chain having 3-carboxy-4-nitrophenylthio group attached thereto thus obtained was found to have a molecular weight of about 32,000 by SDS PAGE. The fact that the heavy chain had 3-carboxy-4-nitrophenylthio group attached thereto was confirmed by measuring the amount of 5-mercapto-2-nitrobenzoic acid formed when 5,5'-dithio-bis(2-nitrobenzoic acid) was caused to act on the protein peak fraction containing the heavy chain of HMW-UK.

REFERENCE EXAMPLE 2

Preparation of plasmin heavy chain

A 300 mg quantity of pure plasminogen obtained from human blood was dissolved in 60 ml of 0.05M Tris HCl buffer (pH=7.8) containing 0.1M NaCl and 25% of glycerol, and 18,000 units of urokinase was added to the solution. Then the mixture was incubated at 25° C. for 8 hours. The mixture was further incubated at 25° C. for 16 hours with addition of 9,000 units of urokinase. To the solution was added a solution of 34 mg of p-nitrophenyl-p-guanidinobenzoate hydrochloride in 0.4 ml of N,N-dimethylformamide (DMF), and the mixture was stirred at 37° C. for 10 minutes and then deoxygenated. 2-Mercaptoethanol was added to the solution to a final concentration of 0.1M, and the resulting solution was stirred at 20° C. for 20 minutes. The solution was then cooled with ice and applied to a lysine-Sepharose column (product of Daiichi Kagaku Yakuhin Co., Ltd., 5 cm in diameter and 15 cm in length) fully equilibrated with deoxygenated 0.01M sodium phosphate buffer (pH=7.2) containing 0.2M NaCl, 0.01M EDTA and 0.001M 2-mercaptoethanol. The column was then washed with the same buffer as above, then washed with 0.01M sodium phosphate buffer (pH=7.2) containing 0.001M 6-aminohexanoic acid, 0.15M NaCl, 0.01M EDTA and 0.001M 2-mercaptoethanol, and thereafter subjected to elution with the same buffer containing 0.003M 6-aminohexanoic acid. The fraction having a peak absorbance at 280 nm was collected and concentrated to 50 ml with use of Diaflo ultrafiltration membrane PM-10 (product of Amicon Corporation) with application of nitrogen pressure. The concentrate was applied to Sephadex G-25 column (product of Pharmacia, 5 cm in diameter and 20 cm in length) previously equilibrated with deoxygenated 0.01M sodium phosphate buffer (pH=7.2) containing 0.15M NaCl and 0.01M EDTA, followed by elution with the same buffer. The fraction having a peak absorbance at 280 nm was collected and concentrated with Diaflo ultrafiltration membrane PM-10 under nitrogen pressure, giving about 100 mg of plasmin heavy chain, which was found to have about 3 moles of SH groups per mole.

EXAMPLE 1

About 1,000,000 units of the urokinase heavy chain (8 ml solution) obtained in Reference Example 1 was admixed with 24 mg of plasmin heavy chain (about 5 ml, as adjusted to a pH of 8 with 1N NaOH) obtained in Reference Example 2, and the mixture was deoxygenated and then stirred at room temperature for 4 hours in a nitrogen stream. Subsequently N-ethylmaleimide was added to the mixture to a final concentration of 1 mM, followed by stirring for 20 minutes. The reaction mixture was concentrated with Diaflo ultrafiltration membrane PM-10. The concentrate was subjected to gel filtration with Sephadex G-150 superfine column (product of Pharmacia, 2.6 cm in diameter and 92 cm in length). The column was equilibrated and subjected to elution with 0.01M sodium phosphate buffer (pH 7.5, containing 0.5M NaCl). The eluate was obtained in 3 ml fractions, which were checked for enzymatic activity by the synthetic substrate method, using S-2444 (AB kabi, Stockholm, Sweden) as the substrate. The fractions of peak activity which appeared to be about 90,000 to about 100,000 in molecular weight were mixed together and concentrated with Diaflo ultrafiltration membrane PM-10. Then phosphate buffered saline was added to the concentrate, and the mixture was concentrated again, and this procedure was repeated 3 times to exchange the buffer. The above process gave about 120,000 units (international units compared with standard urokinase by the synthetic substrate method).

The complex obtained was found to have a molecular weight of about 90,000 to 100,000 by SDS PAGE. When the complex was reduced again and subjected to electrophoresis after treatment with SDS, a band having a molecular weight of about 60,000 and a band with a molecular weight of about 30,000 appeared. This indicates that the complex comprises high molecular weight urokinase heavy chain and plasmin heavy chain coupled therewith in a mole ratio of 1:1 by an S—S bond.

PHARMACOLOGICAL TESTS

(1) Fibrinolytic activity test (a) The complex obtained in Example 1 was tested for lytic activity by the standard fibrin plate method. FIG. 1 shows the resuls.

In FIG. 1, the urokinase activity (unit/ml) (expressed in International Unit/ml against the Japanese Urokinase Standard MM003) determined by the synthetic substrate method is plotted as abscissa and the fibrinolytic activity (expressed in the diameter (mm) of lysis zone) determined by the standard fibrin plate method as ordinate. Line (1) shows the results obtained by the complex of the invention and Line (2) shows the results obtained by HMW-UK (control).

The diagram reveals that the complex of the present invention is much superior to the control, i.e., HMW-UK in fibrinolytic activity.

(b) Plasmin inhibitor prepared from human plasma by the method of M. Moroi et al (J. Biol. Chem., 251, 5956 (1976)) was added in an amount of 0.5 ml to 0.5 ml of the solution containing the present complex or to 0.5 ml of the solution of HMW-UK (control), and each of the mixtures were similarly tested for fibrinolytic activity. Although both mixtures exhibited reduced activities, it was found that the present complex exhibits higher fibrinolytic activity than the control even in the presence of plasmin inhibitor.

(2) Test for ability to be adsorbed by fibrin

The complex of the invention obtained in Example 1 was tested for ability to be adsorbed by fibrin by the following method. A column packed with 3 ml of fibrin-monomer-Sepharose 6B (prepared by the method of D. L. Heene (Thrombosis Research, 2, 137 (1973)) was brought to equilibrium with 0.005M sodium phosphate buffer (pH=7.4) containing 0.135M NaCl. The complex of the invention, HMW-UK, plasminogen or plasmin heavy chain (2 to 3 mg each) dissolved in the same buffer as above was applied to the column, which was then washed with 30 ml of the same buffer as above, followed by elution with the same buffer which further contained 10 mM 6-aminohexanoic acid. The ability to be adsorbed by fibrin was determined in terms of the ratio of recovery of the sample by the eluate fraction. The recovery ratios of plasminogen and plasmin HC were determined based on the absorption of the eluate fraction at 280 nm. Those of the complex of the invention and HMW-UK were determined based on the urokinase activity of the eluate fraction determined by the synthetic substrate method.

The test results show that the complex of the invention has excellent ability to be adsorbed by fibrin.

We claim:

1. A urokinase complex adsorbable by fibrin characterized in that it comprises heavy chain of high molecular weight urokinase as coupled with heavy chain of plasmin by one or more S—S bonds.

2. A urokinase complex as defined in claim 1 wherein about 1 to about 3 moles of the high molecular weight urokinase heavy chain is coupled with 1 mole of the plasmin heavy chain.

3. A urokinase complex as defined in claim 1 wherein about 1 mole of the high molecular weight urokinase heavy chain is coupled with 1 mole of the plasmin heavy chain.

4. A process for preparing a urokinase complex adsorbable by fibrin characterized by coupling heavy chain of high molecular weight urokinase with heavy chain of plasmin by an intermolecular disulfide interchange reaction.

5. A process as defined in claim 4 wherein the intermolecular disulfide interchange reaction is conducted by causing a large excess of 5,5'-dithio-bis-(2-nitrobenzoic acid) to act on the heavy chain of high molecular weight urokinase to obtain a 3-carboxy-4-nitrophenylthio-heavy chain of high molecular weight urokinase and reacting the plasmin heavy chain with the resulting 3-carboxy-4-nitrophenylthio-heavy chain of high molecular weight urokinase.

6. A process as defined in claim 4 wherein the intermolecular disulfide interchange reaction is conducted in a physiological saline or buffer having a pH of about 4 to about 10 at 0° to 40° C. for several minutes to 24 hours, using about 0.5 to about 10 moles of the plasmin heavy chain per mole of the heavy chain of high molecular weight urokinase.

7. A process as defined in claim 5 wherein the intermolecular disulfide interchange reaction is conducted in a physiological saline or buffer having of pH of about 4 to about 10 at 0° to 40° C. for several minutes to 24 hours, using about 0.5 to about 10 moles of the plasmin heavy chain per mole of the 3-carboxy-4-nitrophenylthio-heavy chain of high molecular weight urokinase.

8. A pharmacological composition comprising a urokinase complex adsorbable by fibrin and a pharmacologically acceptable non-toxic carrier, the urokinase complex comprising heavy chain of high molecular weight urokinase and heavy chain of plasmin coupled with the heavy chain of high molecular weight urokinase by one or more S—S bonds.

* * * * *